(12) United States Patent
Scheldrup et al.

(10) Patent No.: US 6,397,850 B1
(45) Date of Patent: Jun. 4, 2002

(54) DUAL-MODE APPARATUS AND METHOD FOR DETECTION OF EMBOLIC DEVICE DETACHMENT

(76) Inventors: Ronald W. Scheldrup, 12 Azalea La., San Carlos, CA (US) 94070; Jason E. Kalgreen, 102 Hoskins Ct. No. 6G, Stanford, CA (US) 94305; Mehran Bashiri, 2010 Eaton Ave., San Carlos, CA (US) 94070

( * ) Notice: Subject to any disclaimer, the term of this patent is extended or adjusted under 35 U.S.C. 154(b) by 0 days.

(21) Appl. No.: 09/501,340

(22) Filed: Feb. 9, 2000

(51) Int. Cl.$^7$ ................................................ A61M 29/00
(52) U.S. Cl. .................... 128/899; 604/93.01; 604/907; 606/191; 606/32
(58) Field of Search .......................... 606/32, 108, 191; 607/1; 600/547; 128/899; 604/27, 36, 57, 59, 60, 73, 93.01, 96.01, 104, 171, 907

(56) References Cited

U.S. PATENT DOCUMENTS

| | | | |
|---|---|---|---|
| 4,739,768 A | | 4/1988 | Engelson |
| 4,884,579 A | | 12/1989 | Engelson |
| 4,994,069 A | | 2/1991 | Ritchart et al. |
| 5,122,136 A | | 6/1992 | Guglielmi et al. |
| 5,250,071 A | | 10/1993 | Palermo |
| 5,354,295 A | | 10/1994 | Guglielmi et al. |
| 5,423,829 A | | 6/1995 | Pham et al. |
| 5,643,254 A | * | 7/1997 | Scheldrup et al. .......... 606/191 |
| 5,669,905 A | | 9/1997 | Scheldrup et al. |
| 5,919,187 A | * | 7/1999 | Guglielmi et al. ............ 606/31 |
| 5,984,929 A | * | 11/1999 | Bashiri et al. .............. 606/108 |

FOREIGN PATENT DOCUMENTS

| | | |
|---|---|---|
| EP | 0 752 235 A1 | 1/1997 |
| WO | WO 95/23558 A1 | 9/1995 |
| WO | WO 00/03643 A1 | 1/2000 |

* cited by examiner

Primary Examiner—Kennedy Schaetzle
(74) Attorney, Agent, or Firm—Lyon & Lyon LLP

(57) ABSTRACT

An apparatus and method are disclosed for accurately detecting the detachment of both electrically conductive and non-conductive implants which have been introduced to and are intended to remain at a desired therapeutic site. The detachment detection apparatus may include a conductive or an electrically-isolated implant, such as a vasoocclusive coil, connected to a wire by an electrolytically severable joint. The detachment assembly further includes a power supply having a direct current drive circuit for supplying a direct current to the joint, an alternating current drive circuit for independently supplying an alternating current to the joint, and an alternating current monitoring circuit for monitoring an alternating current level of the alternating current supplied to the joint. The detection assembly includes a central processing unit for selecting a first mode and a second mode for determining a detachment threshold level indicating detachment of the implant. Additionally, a direct current monitoring circuit is provided for measuring a direct current impedance level of the direct current supplied to the joint wherein a percentage increase in the direct current impedance level indicates detachment of the implant if the alternating current level is greater than the detachment threshold level.

33 Claims, 11 Drawing Sheets

DUAL-MODE APPARATUS AND METHOD FOR DETECTION OF EMBOLIC DEVICE DETACHMENT

TECHNICAL FIELD

This invention is directed to an apparatus and method for detecting detachment of embolic devices and more particularly to detecting detachment of electrically isolated or non-conductive embolic devices.

BACKGROUND ART

Numerous intracranial aneurysms rupture each year in North America. The primary purpose of treatment for a ruptured intracranial aneurysm is to prevent rebleeding. There are a variety of approaches to treat ruptured and non-ruptured aneurysms including, for example, delivering an embolic device through an endovascular catheter. In this approach, the interior of the aneurysm is entered by use of a catheter such as those shown in Engelson (Catheter Guidewire), U.S. Pat. No. 4,884,575 and also in Engelson (Catheter for Guidewire Tracking), U.S. Pat. No. 4,739,768. These patents describe devices utilizing guidewires and catheters which allow access to an aneurysm from remote portions of the body. Specifically, by the use of catheters having very flexible distal regions and guidewires which are steerable to the region of the aneurysm, embolic devices which may be delivered through the catheter are an alternative to the extravascular and extra-intravascular approaches.

The endovascular approach typically includes two major steps. The first step involves the introduction of the catheter to the aneurysm site using devices such as shown in the Engelson patents. The second step often involves filling the aneurysm in some fashion or another. For instance, a balloon may be introduced into the aneurysm from the distal portion of the catheter where it is inflated, detached, and left to occlude the aneurysm. In this way, the parent artery is preserved. Balloons are becoming less in favor because of difficulty in introducing the balloon into the aneurysm sac, the possibility of an aneurysm rupture due to overinflation of the balloon within the aneurysm or due to stress placed on the nonspherically shaped aneurysm by the spherical balloon, and the risk associated with traction produced when detaching the balloon.

A highly desirable embolism-forming device that may be introduced into an aneurysm using endovascular placement procedures, is found in U.S. Pat. No. 4,994,069, to Ritchart et al. The device—typically a platinum/tungsten alloy coil having a very small diameter—may be introduced into an aneurysm through a catheter such as those described in Engelson above. These coils are often made of wire having a diameter of 2–6 mils. The coil diameter may be 10–30 mils. These soft, flexible coils may be of any length desirable and appropriate for the site to be occluded. For instance, the coils may be used to fill a berry aneurysm. Within a short period of time after the filling of the aneurysm with the embolic device, a thrombus forms in the aneurysm and is shortly thereafter complemented with a collagenous material which significantly lessens the potential for aneurysm rupture.

Coils such as seen in Ritchart et al. may be delivered to the vasculature site in a variety of ways including, e.g., mechanically detaching them from the delivery device as is shown in U.S. Pat. No. 5,250,071, to Palermo or by electrolytic detachment as is shown in Guglielmi et al. (U.S. Pat. No. 5,122,136), discussed below.

Guglielmi et al. shows an embolism-forming device and procedure for using that device. Specifically, the Guglielmi device fills a vascular cavity (such as an aneurysm) with an embolic device, typically a platinum coil, that has been endovascularly delivered. The coil is then severed from its insertion tool by the application of a small electric current. Desirably, the insertion device involves a guidewire which is attached at its distal end to the embolic device by a sacrificial joint that is electrolytically dissolvable. Guglielmi et al. suggests that when the embolic device is a platinum coil, the platinum coil may be 1–50 cm. or longer as is necessary. Proximal of the embolic coil is a guidewire, often stainless steel in construction. The guidewire is used to push the platinum embolic coil, obviously with great gentleness, into the vascular site to be occluded. The patent shows a variety of ways of linking the embolic coil to the pusher guidewire. For instance, the guidewire is tapered at its distal end and the distal tip of the guidewire is soldered into the proximal end of the embolic coil. Additionally, a stainless steel coil is wrapped coaxially about the distal tapered portion of the guidewire to provide column strength to the guidewire. This coaxial stainless steel wire is joined both to the guidewire and to the embolic coil. Insulation may be used to cover a portion of the strength-providing stainless steel coil. This arrangement provides for two regions which must be electrolytically severed before the embolic coil is severed from the guidewire.

U.S. Pat. No. 5,423,829 to Pham et al. describes a variation of the Guglielmi detachable coil using an improved sacrificial link between the guidewire and the coil. The size of the sacrificial link is limited to allow more precise placement of the embolic device and facile, quick detachment. The focussed electrolysis found at the sacrificial site reduces the overall possibility of occurrence of multiple electrolysis sites and liberation of large particles from those sites.

Previous attempts to detect the detachment of a coil from, for example, a core wire generally involved a direct current (DC) constant current circuit with a DC voltage monitor to measure DC impedance. The circuit generally included a DC constant current power source having its positive terminal coupled to an electrolytically severable joint or sacrificial link via the core wire. DC current supplied to the joint electrolytically dissolves the sacrificial joint, thereby detaching the coil. The negative terminal of the power source typically was coupled to the patient's skin via a large skin electrode (e.g., a ground pad or needle). Other grounding arrangements include providing an embolic device delivery microcatheter with a cathode that is electrically coupled to the negative terminal of the power source (see U.S. Pat. No. 5,354,295 to Guglielmi et al.). However, the actual moment of detachment of the occlusion device using these schemes may go undetected because detachment of the coil sometimes occurs without a corresponding significant increase in measured DC impedance.

When longer detachment zones are employed, it has been observed that the actual point of detachment may occur anywhere along the zone. Where the erosion via electroysis occurs distally in that zone, the impedance does not always change.

Accordingly, a DC constant current and monitoring scheme that monitors impedance may not detect the precise moment of detachment if the detachment does not occur exactly at the most proximal point on the sacrificial link. Thus, for these variations of the Guglielmi detachable coils, these schemes do not provide the desired repeatability or accuracy in detecting detachment. When detachment goes undetected, one is unable to precisely determine when the system's power should be shut down or the pusher wire removed. The time required for the procedure may be unintentionally increased. In addition, particles may be liberated into the blood stream after coil detachment has occurred.

U.S. Pat. Nos. 5,643,254 and 5,669,905 to Scheldrup et al. disclose another method for predictably determining the instant of electrolytic detachment of an embolic device. According to these patents, DC power with alternating current (AC) superposition or modulation is supplied to a sacrificial link or joint. The AC impedance (as measured by the amplitude of the superimposed AC signal) is monitored. When a predetermined change in monitored AC impedance occurs, indicating coil detachment, the DC power is interrupted to minimize or avoid further electrolysis.

With the advent of new types of electrolytically detachable embolic assemblies in which the occlusive device is electrically isolated or non-conductive such as those described in U.S. Pat. No. 5,984,929 to Bashiri et al., the entirety of which are hereby incorporated by reference, these known detection systems can be inadequate. For example, if the detachment zone comes into contact with the electrically isolated coil or a previously detached coil, or if the electrically isolated coil folds back on itself and contacts the detachment zone, the amplitude or signal level corresponding to the superimposed AC impedance will drop to a clearly lower value. While the drop in amplitude does not present a problem in and of itself, if this unintended contact is broken, the subsequent increase in AC impedance, and hence, monitored AC signal level may be interpreted as coil detachment even though the coil may still be attached.

Although an operator may become facile with using such detection devices in connection with non-conductive or electrically isolated coils, if for some reason the operator is unaware or unsure if the coil being detached is electrically isolated or of a previous generation electrically conductive vintage, it may be difficult or impossible for the operator to tell when coil detachment takes place.

Thus, there is a need for a system or assembly that accurately detects detachment of various occlusion devices including electrically isolated or non-conductive occlusion devices.

In addition, previous generation detection systems or assemblies are integrated with power supply controllers incapable of providing additional safeguards to ensure that the patient is not risk. For example, previous generation power supply controllers lack various features including: automatic calibration of the current levels, independent AC and DC circuitry, automatic reduction in DC current, automatic current ramp up, and automatic data storage during detachment procedures.

Thus, there is still a need for a power supply controller that overcomes these and other shortcomings in detecting the detachment of embolic devices.

SUMMARY OF THE INVENTION

This invention is an apparatus and method for detecting the detachment of implants which have been introduced to and are intended to remain at the desired therapeutic site. The detachment detection assembly can include a conductive or an electrically-isolated implant, such as a vasoocclusive coil, connected to a wire by an electrolytically severable joint. The detachment assembly further includes a power supply having a direct current drive circuit for supplying a direct current to the joint, an alternating current drive circuit for independently supplying an alternating current to the joint, and an alternating current monitoring circuit for monitoring the level of alternating current supplied to the joint. The detection assembly includes a central processing unit for selecting a first mode and a second mode for determining a detachment threshold level indicating detachment of the implant.

Additionally, a direct current monitoring circuit is provided for measuring an output voltage of the direct current drive circuit wherein a percentage increase in the output voltage indicates detachment of the implant if the alternating current level is greater than the detachment threshold level.

DETAILED DESCRIPTION

Figure 1:
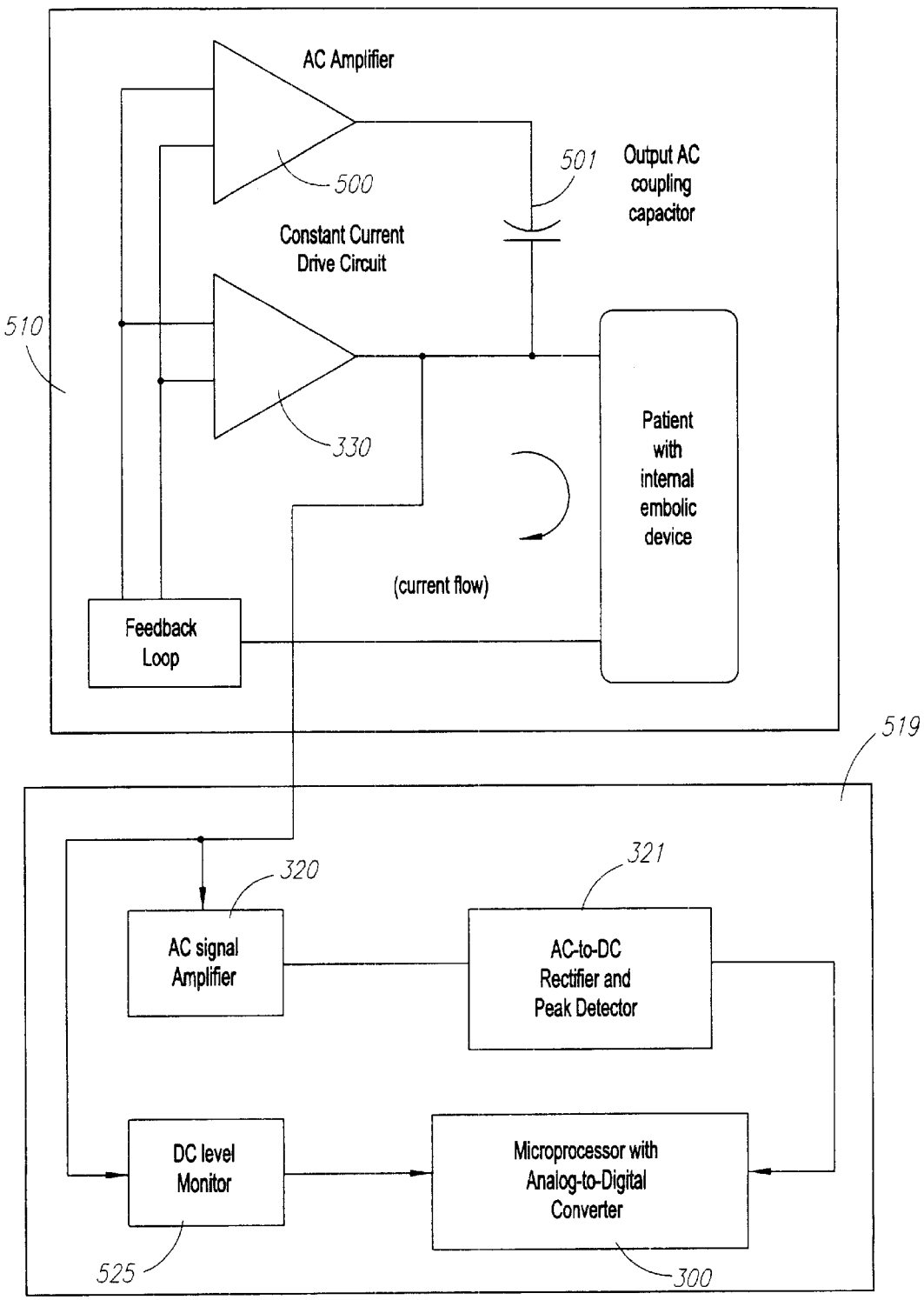
FIG. 1 is a block diagram of a power supply and detection circuit for detecting electrolytic separation of a vasoocclusive device in accordance with the principles of the present invention.

Referring now to FIG. 1 where like numerals refer to like elements, a constant current drive circuit 510 and a detachment detection circuit (or an embolic device detection circuit, hereafter "EDDC") 519 in accordance with the present invention are shown. The EDDC 519 includes an alternating current (AC) impedance monitoring circuit and may also include a microprocessor 300, both of which will be described in more detail below. The apparatus or system diagrammatically shown in FIG. 1 can be used in conjunction with various occlusive devices such as, but not limited to, coils, stents, vena cava filters, or any mammalian implant capable of deployment by electrolytic means.

In addition, the inventive assembly shown in FIG. 1 may be used in conjunction with both electrically conductive implants as shown in U.S. Pat. No. 5,122,136 to Guglielmi et al. as well as electrically isolated or non-conductive implants as shown in U.S. Pat. No. 5,984,929 to Bashiri et al., both of which are hereby incorporated by reference in their entirety.

Electrically Conductive Implants

Figures 2, 3:
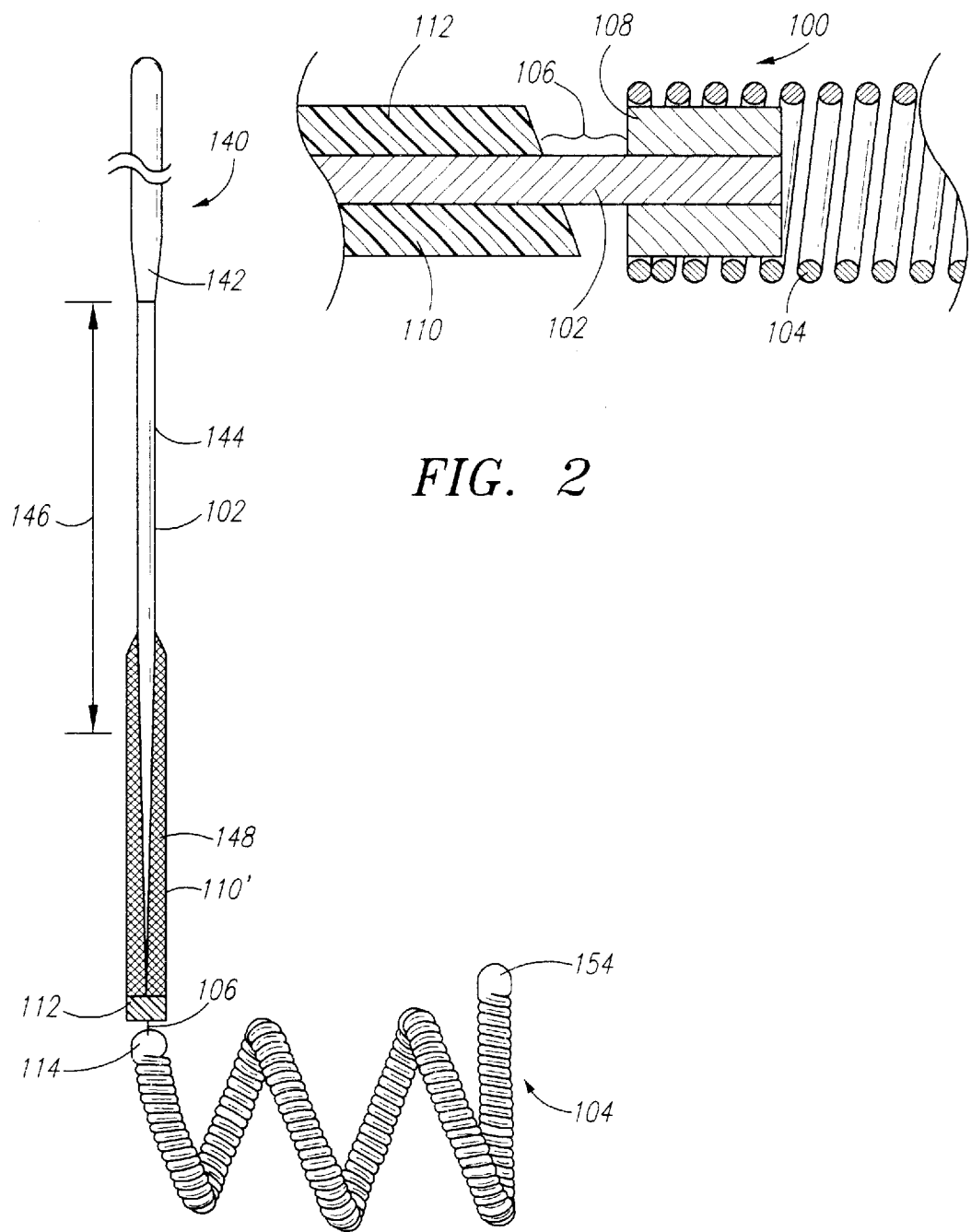
FIG. 2 is a partial longitudinal cross-section of a solderless electrolytically susceptible, sacrificial link between a core wire and an vasoocclusive device.
FIG. 3 is a partial longitudinal cross-section of a core wire assembly for use with the present invention.

Referring now to FIG. 2, an example of an electrically conductive implant is shown. As shown in FIG. 2, a vasoocclusive device 104 is joined to core wire 102 via a sleeve 108. In this example, sleeve 108 electrically connects core wire 102 to implant 104 which, when a vasoocclusive coil, is typically made of an electrically conductive and radiopaque physiologically compatible material such as platinum, tungsten, gold, iridium, or alloys of these. Thus, when current is supplied to core wire 102, the current also flows to electrically conductive implant 104. For this reason, the implant itself may be considered "electrically conductive".

While the implant 104 is electrically connected to core wire 102, most of the current is directed to a sacrificial joint 106. This is because core wire 102 is generally covered with an insulating material such as TEFLON, polyurethane, polyethylene, polypropylene, or other suitable polymeric material except for the most distal exposed joint or sacrificial link 106. Joint 106 is not coated with an electrical insulator and is of a material which is more susceptible to electrolytic dissolution in blood than implant 104 and sleeve 108. For example, joint 106 may be stainless steel. The core wire 102 is typically stainless steel and may be disposed within a protective catheter (not shown). Core wire 102 typically is approximately 10–30 mils in diameter. Often the core wire is 50–300 cm in length, that is to say from the entry site outside the body to sacrificial link 106.

Electrolytically severable joint 106 is a discrete link. By "discrete" we mean to say preferably that the joint is substantially dissolved upon release of the vasoocclusive device 104. Alternatively, "discrete" may mean that the length of the link 106 is no greater than the diameter of the sacrificial link 106 or that the electrolytic surface present after the vasoocclusive device is released is not substantially greater than would be a circle having the diameter of the sacrificial link 106. For instance, it may be as short as 0.010 inches, and typically is no longer than 0.150 inches in length.

As shown in FIG. 2, vasoocclusive device 104 may be placed upon a sleeve 108 as previously described which is of a material more noble than the material found in core wire 102. The sleeve 108 need not be of the same material as is the detachable device or member 104. It simply requires that the sleeve 108 not decompose prior to core wire 102.

In FIG. 2, the electrically conducing vasoocclusive device 104 is shown to be a coil. It may, however, be a coil or a braid or other vasoocclusive device as is already known. The vasoocclusive device may be covered or connected with fibrous materials tied to the outside of the coil or braided onto the outer cover of the coil as desired. Such fibrous adjuvants may be found in U.S. Pat. No. 5,382,259 to Phelps et al., or in U.S. Pat. No. 5,226,911 to Chee et al. entitled "Vasoocclusion Coil with Attached Fibrous Elements", the entirety of which are each hereby incorporated by reference.

FIG. 3 shows a typical layout using a discrete electrolytically severable joint 106 as was generally shown in FIG. 2 above. In FIG. 3, a conventional insulated (perhaps with TEFLON or other similar polymer) stainless steel core wire assembly 102 may be placed within a catheter. As was noted above, stainless steel core wire generally has a diameter of approximately 10–30 mils. In the embodiment of FIG. 3, core wire assembly 140 is tapered at its distal end to form a conical section 142 which joins a further section 144 which extends along a length of core wire 146. Section 144 then gradually narrows down to a thinner section 148. The core wire assembly 140, as noted above, may be placed within a catheter body and is typically 50–200 cm. in length down to sacrificial link 106. The distal section of core wire assembly 140 may have an outer TEFLON sleeve (or sleeve of other appropriate insulating material). Furthermore, it has an end plug 112 to permit isolation of the core wire electrically from the blood except at sacrificial discrete link 106. The proximal end of vasoocclusive device 104 may be joined to core wire as described above. Preferably, vasoocclusive device 104, when a coil, forms a secondary loop after it emanates from the end of the catheter. The distal end of vasoocclusive device 104 may also have an end plug or tip to prevent punctures of the aneurysm when introduced into the aneurysm sac.

Coil or vasoocclusive device 104 may be pre-biased to form a cylinder, a conical, or other desired envelope. However, the vasoocclusive device 104 is extremely soft and its overall shape is easily deformed. When inserted within the catheter (not shown), the vasoocclusive device 104 is easily straightened to lie axially within the catheter. Once ejected from the tip of the catheter, vasoocclusive device 104 may form a shape shown in FIG. 3 or may be loosely deformed to conform to the interior shape of the aneurysm.

Deploying Electrically Conductive Implants

Figure 4:
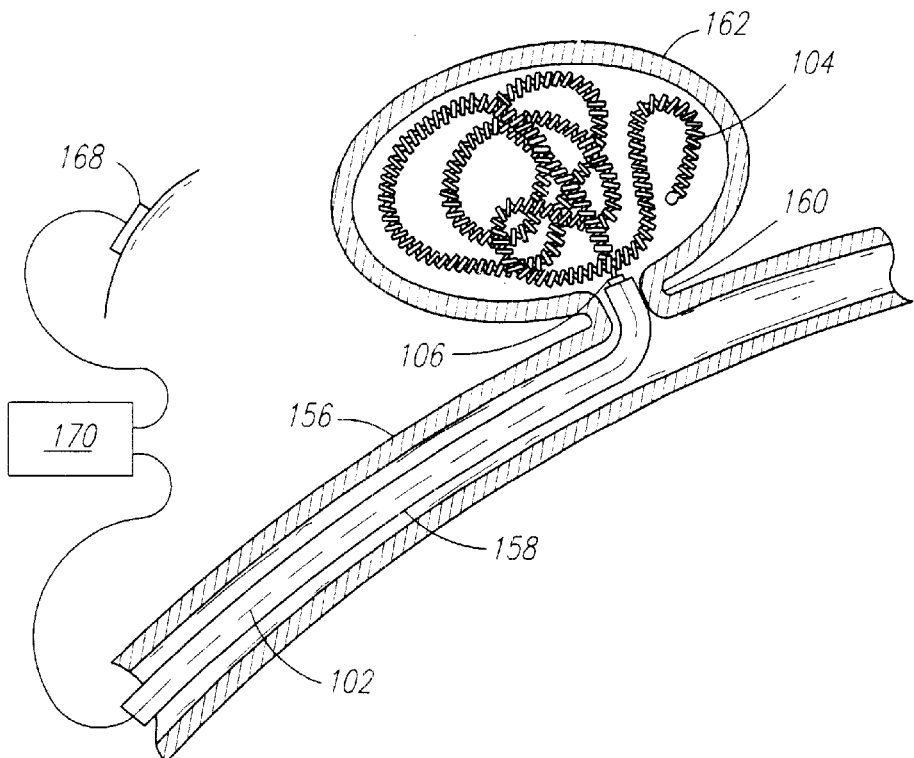
FIGS. 4 and 5 schematically depict the method for deploying a vasoocclusive device according to the present invention.
Figure 5:
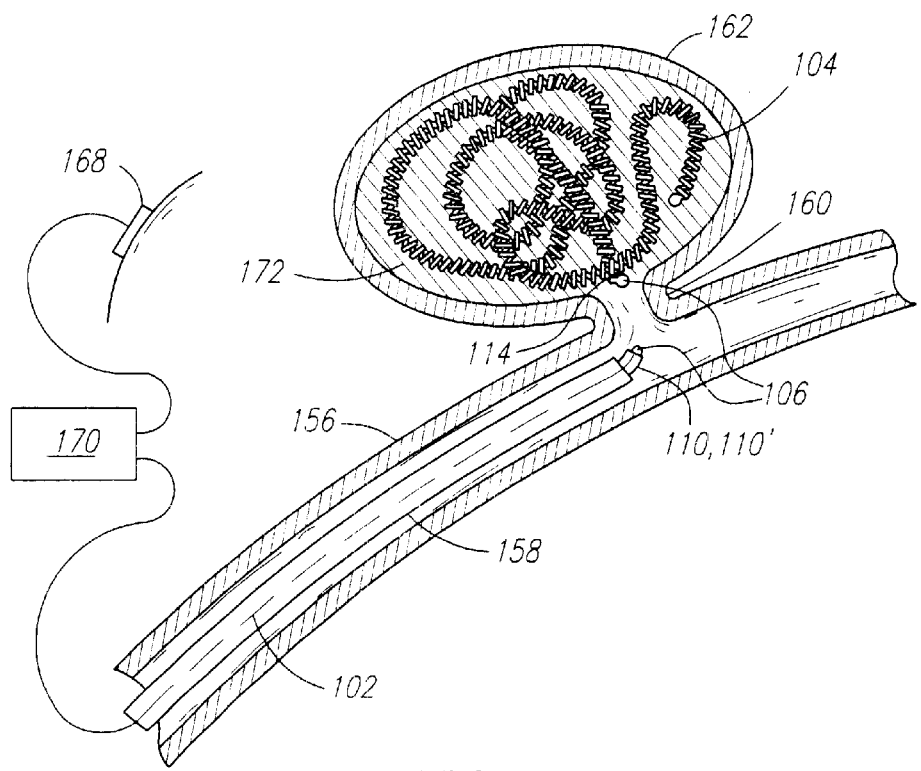

FIGS. 4–5 show the procedure of introducing or deploying a vasoocclusive coil using the method described in Guglielmi et al. above.

For example, FIG. 4 shows the placement of an occlusion device described above within an aneurysm. The process of placing an embolic device is typically practiced under fluoroscopic control with local anesthesia. A transfemoral catheter is utilized to treat a cerebral aneurysm and is usually introduced at the groin. The physician guides the distal tip of the catheter to the target site. The embolic device is then inserted into the catheter. Using a fluoroscope, the physician guides the device to the desired position before separation is initiated. When the vasoocclusive device 104 is platinum, it is not effected by electrolysis. When the guidewire and pertinent portions of the supporting coils at the distal tip of the guidewire are insulated, only the exposed portion at the sacrificial link 106 is effected by the electrolysis.

In FIG. 4, catheter 158 is positioned in a vessel 156 with the tip of catheter 158 placed near neck 160 of aneurysm 162. A vasoocclusive implant, such as device 104, is fed into aneurysm 162 at least until sacrificial link 106 is exposed beyond the distal tip of the catheter 158. A positive electric current of approximately 0.1–10 mA, preferably about 1 mA, at 0.1–6.0 volts, is applied to core wire 102 (shown in dashed line) to dissolve sacrificial link 106. Power supply controller 170 provides DC power with AC superposition as will be discussed in more detail below.

Referring to FIGS. 4 and 5, the positive terminal of power supply 170 is attached to the proximal end of core wire 102. A negative or return electrode 168 is coupled to the negative terminal of power supply 170. Electrode 168 is typically placed in electrical contact with the skin. Alternatively, the electrode can comprise a ground wire with a skin patch located behind the shoulder of the patient may be used. In addition, assemblies such as those disclosed in U.S. patent application Ser. No. 09/026,373 to Wheelock et al., the entirety of which is hereby incorporated by reference, in which the device itself forms a return path for the electrolytic current, obviating the need for a skin patch, may be used as well.

After a vasoocclusive device has been properly placed inside the aneurysm 162, the device 104 is detached from core wire 102 by electrolytic disintegration of electrolytically severable joint 106. After electrolytically severable joint 106 is completely dissolved by electrolytic action, typically within 30 seconds to a few minutes, the core wire 102 is removed from catheter 158 and from vessel 156. Additional vasoocclusive devices may be placed in aneurysm 162 along with previously detached devices 104 until aneurysm 162 is occluded as shown in FIG. 5. At this point, guidewire 102 and catheter 158 are withdrawn.

Prior to withdrawing the core wire, however, the time of detachment must be accurately ascertained in order to ensure that the implant has in fact detached. Failure to accurately determine detachment may even put the patient at risk if the core wire is prematurely withdrawn.

Detecting Detachment of Electrically Conductive Implants

Examples of known detection systems for detecting detachment of electrically conductive implants are generally shown in FIGS. 6–10. In general terms, these systems supply a steady electrolyzing direct current to the electrolytically severable joint, supply an alternating current superimposed on the direct current to the joint, monitor the alternating current impedance, and signal coil detachment when the monitored alternating current impedance increases more than a specified percentage of itself averaged over a period of time.

Figure 6:
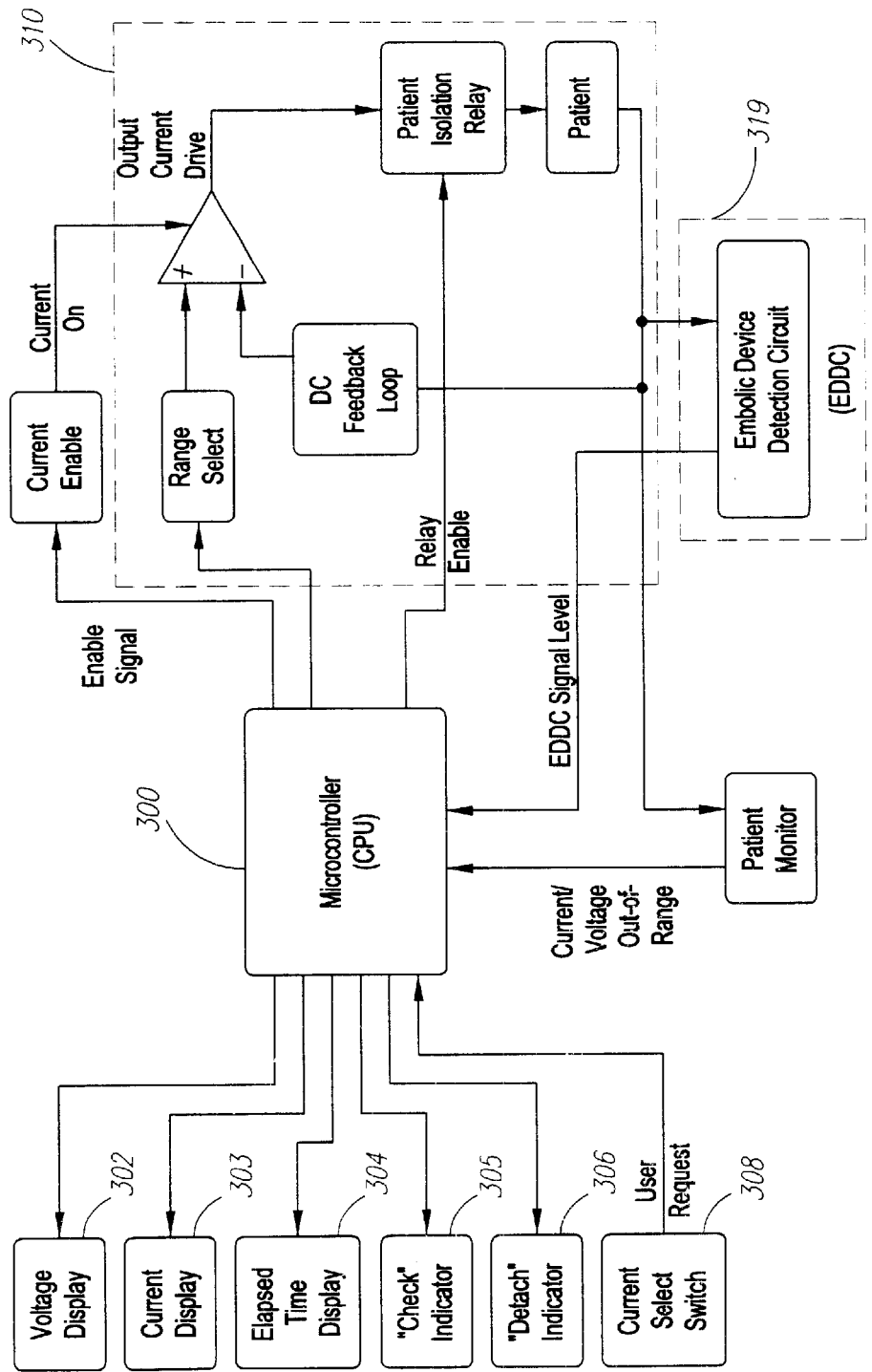
FIG. 6 is a block diagram showing a power supply and detection circuit for detecting detachment of an electrically conductive vasoocclusive implant integrated with a power supply controller.

Referring now to FIG. 6, a known system for detecting detachment of electrically conductive implants is shown. It includes a power supply 310 and detection circuit 319 integrated with a power supply controller. In addition, FIG. 6 shows a number of individual components, each of which will be briefly described below.

First, the voltage display 302 displays the voltage required to maintain the current flowing through the joint and the patient. In Pause Mode, that is, when electrolytic separation has occurred, and the unit has shut off power to the core wire, the display shows the voltage immediately prior to coil detachment. The current display 303 displays the actual current flowing through the linking member and the patient. In addition, the display briefly flashes the new current setting when the current select switch 308 is pressed or when power-up occurs, and then returns to the continuous display of actual current. In Pause Mode, the display shows the current immediately prior to coil detachment. In Normal Mode, the current-select switch 308 is used to change the current setting. The current may be changed by the physician at any time. Each time the switch is pressed, the current display 303 briefly flashes the new current setting. In Pause Mode, pressing the current-select switch 308 will resume Normal Mode. The current and voltage displays 303 and 302 resume the real-time display of these parameters and the elapsed time display 304 resumes counting from where it was paused.

The elapsed time display 304, typically, though not necessarily, displays the elapsed time from the start of the procedure. The check indicator 305, which can be a light, audible alarm, or the like, is activated when the microprocessor and embolic device detection circuit (EDDC) 319 determine that coil detachment has occurred, indicating that the power supply has entered Pause Mode. The detach indicator 306, which can be light, audible alarm, or the like, is activated when the power supply is in Pause Mode after detecting a coil detachment. In each case, the physician is instructed to check detachment using fluoroscopy. In Pause Mode, display 304 will therefore show the amount of time required to detach the coil.

Central processing unit (CPU) 300 controls and monitors vital functions of the power supply. However, other processors may be used as would be apparent to one of ordinary skill. In the illustrated embodiment, CPU 300 is used to monitor output DC voltage and current, elapsed time, and requests for changing the DC current. The CPU is outside the critical path of the current control loop, which is implemented in hardware. The CPU manages the displays, status indicators and beeper, runs self-diagnostic tests at power-on, issues current setting changes and the fail-safe current enable signal, monitors the EDDC 319 signal to determine when coil detachment has occurred, and monitors the current-select switch.

Figure 7:
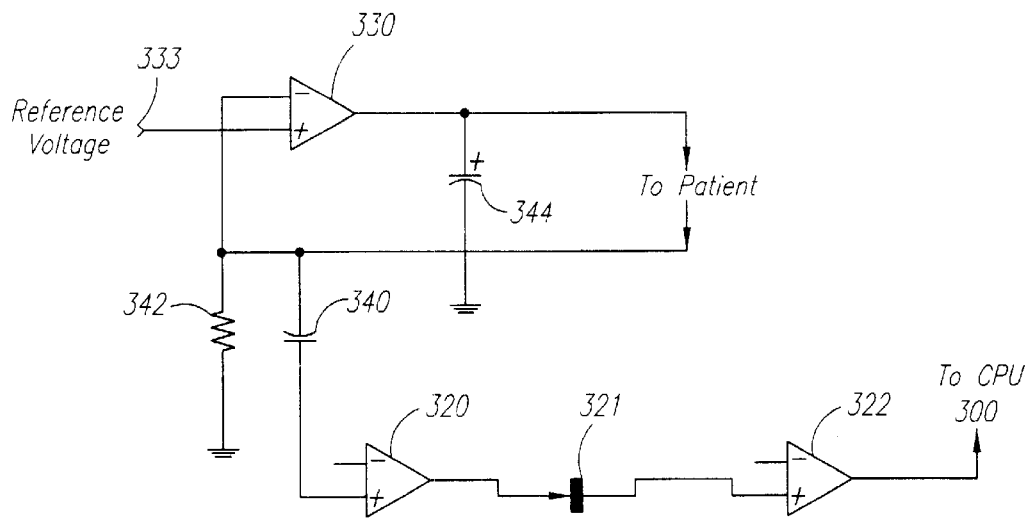
FIG. 7 is a schematic representation of the power supply and detection circuit of FIG. 6.

The construction of an EDDC is shown in FIG. 7. Amplifier 330 provides a constant current output. The constant current output may be, for example, 0.5 or 1.0 mA. Resistor 342 is connected between the inverting input terminal of amplifier 330 and ground and ensures the maintenance of the constant current flow from amplifier 330. When the constant current amplifier 330 has achieved equilibrium, i.e., when the output current exactly matches the setpoint present at the non-inverting input terminal, the amplifier will oscillate at approximately 20 to 24 kilohertz (kHz) at an amplitude of several hundred millivolts due to a lagging error correction signal (out-of-phase feedback). That is, the amplifier 330 provides constant DC current with AC superposition. The amplitude of this AC signal is dependent on the bandwidth characteristics of the constant current amplifier and the AC impedance of the implant assembly and of the patient's body.

In the EDDC of FIG. 7, the AC feedback signal through the patient's body passes through capacitor 340 (e.g., in this case, a 0.1 microfarad monolithic capacitor). The AC signal is then amplified in the AC signal amplifier 320, rectified in the AC to DC rectifier 321 and the resulting DC signal is further amplified in DC amplifier 322. The amplified DC signal, the level of which is representative of the amplitude of the error correction voltage of constant current amplifier 330 is then sent to the microprocessor (CPU) 300 for monitoring and analysis. The AC signal, therefore, is monitored by monitoring the level of the amplified DC signal which may be monitored about every 10 to 250 milliseconds, preferably about every 50 to 200 milliseconds, and constantly averaging the signal about every 5 to 50 samples, preferably about every 10–20 samples or about every 0.5–10 seconds, preferably about every 2–6 seconds. In this manner, the CPU can accurately determine the instant the electrically conductive embolic device detaches. When the embolic device detaches, constant current amplifier 330 is no longer in equilibrium and instantly reacts to the change in AC impedance. During the next several dozen milliseconds, amplifier 330 makes large corrections to the DC output voltage to maintain the set current, which disrupts the stable self-oscillation feedback. In other words, the change in AC impedance upsets the balance of the amplifier circuit, and the amplitude of the self-oscillation signal is affected. During this period the amplified EDDC signal will show a sudden voltage change of greater than 10%, preferably a change of greater than 20% of the average level for the procedure. This sudden voltage change detects the dissolution of the junction between the conductive embolic implant and the core wire. When the sudden voltage change is detected, the microprocessor immediately halts current flow and indicates to the physician that implant detachment has occurred.

In sum, the detection system as shown in FIGS. 6–7 involves placing an electrically conductive vasoocclusive device with a sacrificial link at a desired site in a mammal via a delivery member (such as a core wire), supplying DC power with AC superposition to the sacrificial link, monitoring the amplitude of the AC signal (which could be voltage or current averaged over a time period) and detecting any sudden percentage change in that signal. The detection system further involves interrupting the DC power input in response to detecting such a sudden change in the AC signal. Thus, reliable detection of detachment of electrically conductive coils from a core wire may be achieved.

Detecting Detachment of Conductive Implants Using External AC Source

Figure 8:
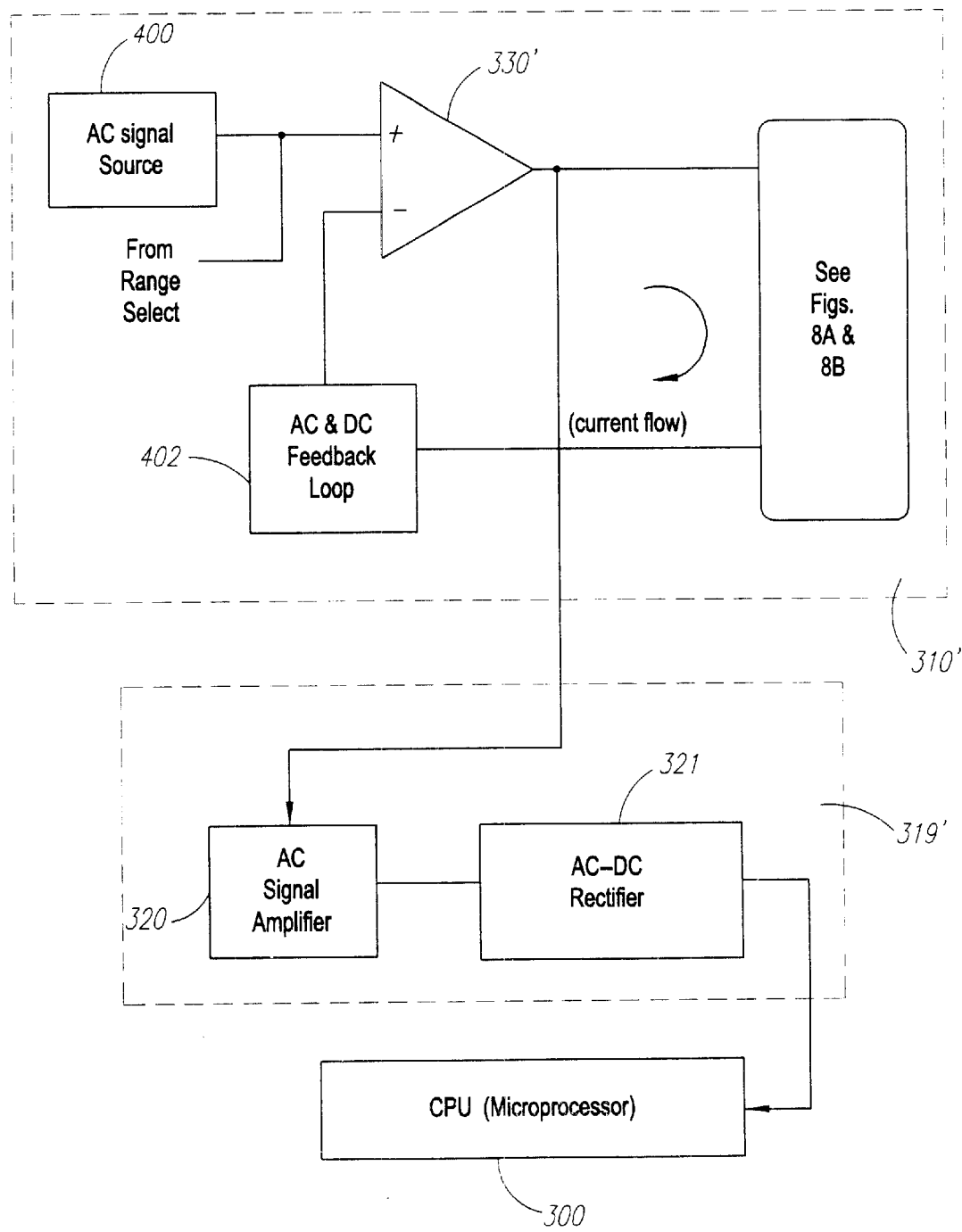
FIG. 8 is a block diagram of another power supply and detection circuit for detecting detachment of electrically conductive vasoocclusive implants.
Figure 9:
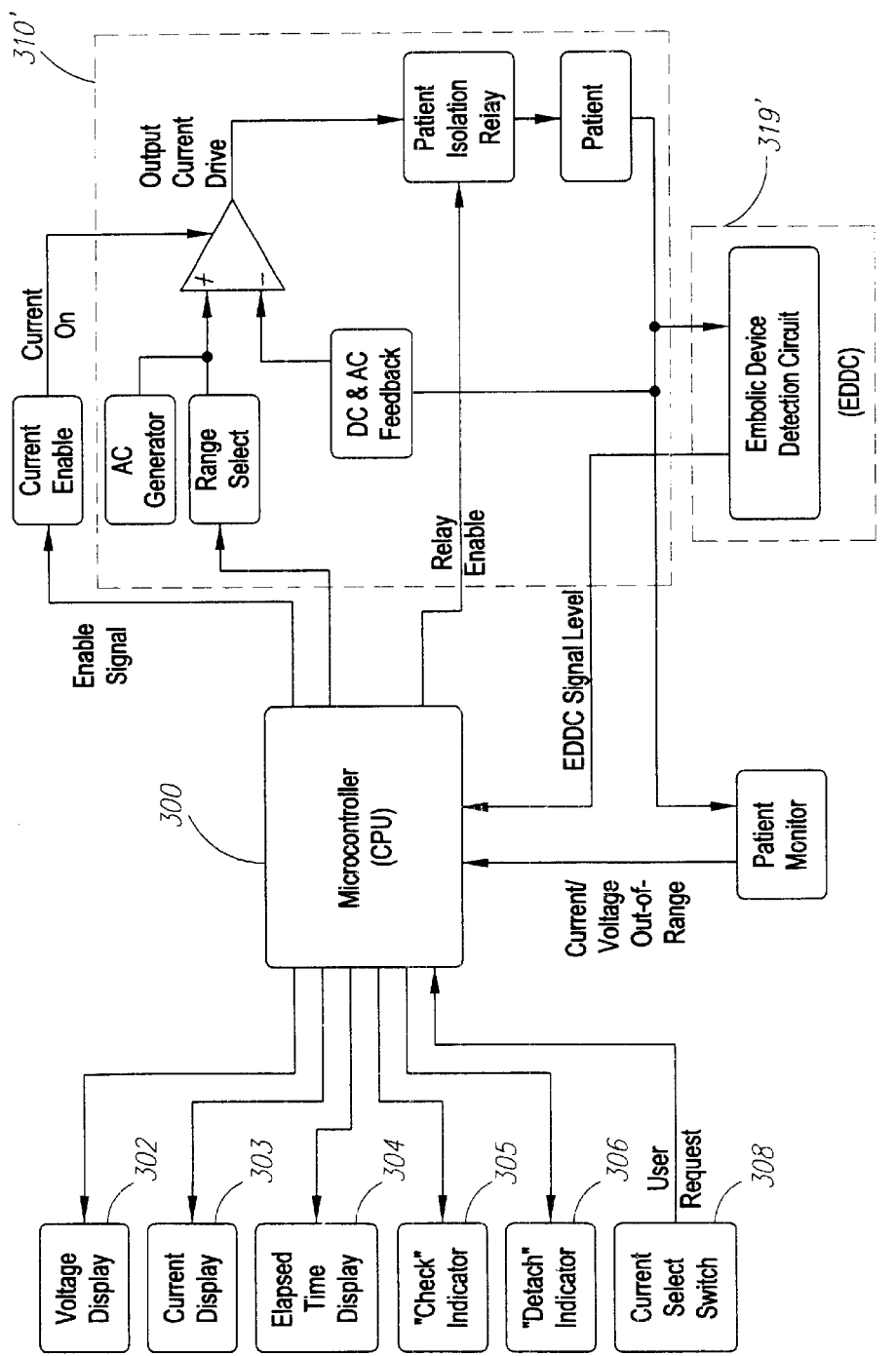
FIG. 9 is a block diagram showing the assembly of FIG. 8 integrated with a power supply controller.
Figure 10:
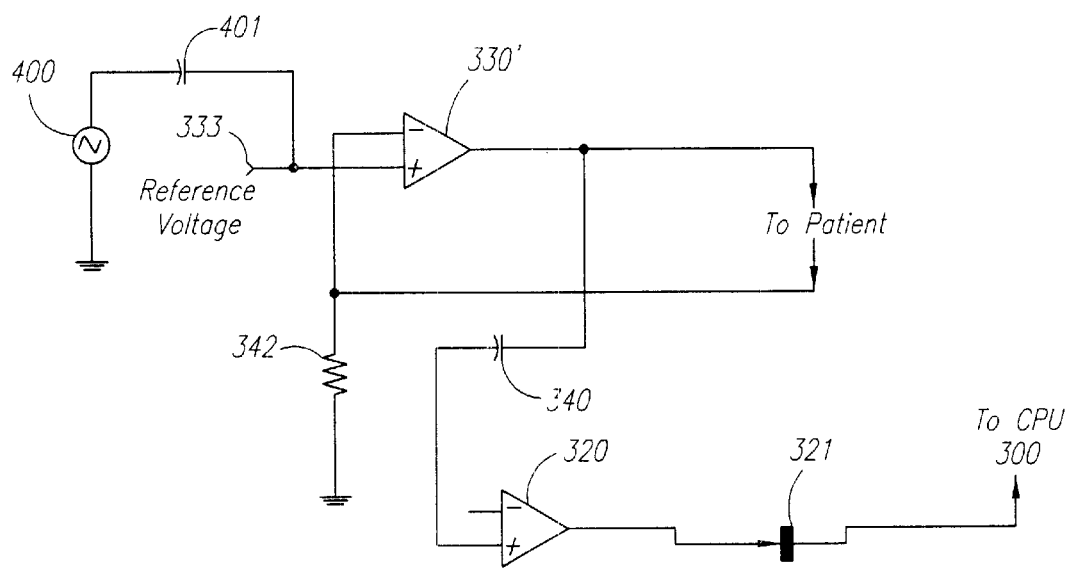
FIG. 10 is a schematic representation of the block diagram of FIG. 8.

Turning now to FIGS. 8–10, another known variation of an electrically conductive implant detachment detection system is shown. Like the previous example, this detachment detection system generally includes supplying a steady electrolyzing direct current to the electrolytically severable joint, supplying an alternating current superimposed on the direct current to the joint, monitoring the alternating current impedance, and signaling coil detachment when the monitored alternating current impedance changes more than a specified percentage averaged over a period of time.

However, the FIG. 8 power supply 310' and detection circuit 319' differ from those shown in FIGS. 6–7 in that an external AC signal source 400 is added, an AC and DC feedback loop 402 is substituted for the DC feedback loop of FIG. 6, DC level amplifier 322 of FIG. 7 is no longer present, and the input to AC signal amplifier 320 comes from the output of the power delivery amplifier (as opposed to from the previous DC feedback loop). With this arrangement, one directly monitors the AC impedance by observing the reaction of amplifier 330' in response to the change in AC impedance.

Referring to FIG. 9, the power supply 310' and detection circuit 319' are shown integrated with a power supply controller. The operation of the power supply controller in. FIG. 9 is the same as described for FIG. 6 except that an external AC generator is provided. The AC generator is part of the power supply circuit 310' and is discussed below.

The construction of the power supply delivery circuit 310' and the EDDC 319' are shown in FIG. 10. In FIG. 10, AC signal source 400 is capacitively coupled to the reference input of amplifier 330' so as to modulate the output current (i.e., provide AC superposition on the DC current). Capacitor 401 is provided between AC signal source 400 and amplifier 330' to isolate DC bias from the AC signal input. The operation of the constant current source (schematically shown in FIG. 10) is the same as that described with reference to FIG. 7.

In operation, an AC signal from source 400 is provided to the non-inverting input of amplifier 330' where it is summed with the DC current reference 333. DC current with AC superposition is output from amplifier 330' and sent to the sacrificial link (e.g., link 106 of FIG. 2). The AC signal is monitored at the output of the constant current amplifier 330' where a measurement of AC impedance can be made through EDDC 319'. More specifically, the amplitude of the AC signal is monitored through pick-off capacitor 340. The AC signal from capacitor 340 is then amplified in the AC signal amplifier 320, and is rectified and peak detected in the AC to DC rectifier 321. The DC signal, the level of which is representative of the amplitude of the output AC voltage of constant current amplifier 330' is then sent to the microprocessor (CPU) 300 for monitoring and analysis.

One advantage of the position of this AC signal monitoring point is that the amplitude of the AC signal is higher than in the arrangement of FIG. 7, therefore eliminating the need for additional amplification by amplifier 322 as shown in FIG. 7.

The AC signal, which in the illustrated embodiments is voltage, is monitored by sampling the level of the rectified DC signal every 50 to 1000 milliseconds, preferably every 100 to 500 milliseconds, and constantly averaging the signal over the most recent 5 to 50 samples, preferably the most recent 20–40 samples, or every 0.5–10 seconds, preferably every 1–2 seconds. In this manner, the CPU accurately determines the average AC impedance level of the electrically conductive occlusion device. When the electrically conductive occlusion device detaches, constant current amplifier 330' reacts to the change in AC impedance. The amplitude of the AC waveform increases to maintain the constant AC current set at the non-inverting input. During this period the EDDC signal will show a sudden voltage increase of greater than 20%, preferably an increase of greater than 30% of the average level for the procedure. This sudden voltage increase detects the dissolution of the junction between the electrically conductive embolic device and the core wire.

While the above implant detachment detection systems may reliably detect detachment of electrically conductive implants, these known systems may misdiagnose detachment of electrically isolated or non-conductive coils, as is discussed below. Accordingly, what is needed is a detection system that may accurately detect the detachment of both electrically conductive and electrically isolated implants.

Electrically Isolated Or Non-Conductive Implants

In addition to detecting detachment of the electrically conductive embolic devices described above, the detection system of the present invention is capable of detecting detachment of electrically-isolated or non-conductive implants.

Figure 11:
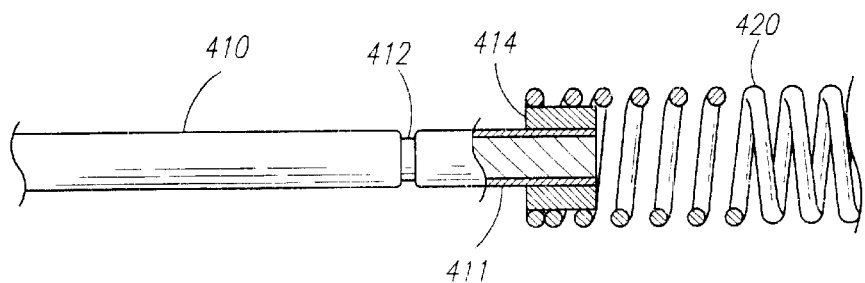
FIG. 11 is a partial longitudinal cross-section of an electrically isolated implant coupled to a core wire.

Examples of electrically isolated implants are described in, for example, U.S. Pat. No. 5,984,929 to Bashiri et al., the entirety of which is incorporated by reference. One example of an electrically isolated implant is illustrated in FIG. 11. In FIG. 11, the electrically isolated coil 420, which is typically platinum, is coupled to a core wire 410 which has an electrolytically severable joint 412. Core wire 410 has an insulating layer 411 preventing electrical contact between the coil 420 and the core wire, thereby electrically isolating the coil from the current supplied to the core wire.

An advantage of electrically isolating the coil is that the DC current is prevented from flowing to the coil, thereby forcing most or all of the DC electrolyzing current to the detachment zone or electrolytically severable joint 412. Consequently, overall detachment times are reduced and there is less variability between coil detachment times. For these and other advantages, the electrically isolated implants have gained favor among users, creating a need to accurately detect detachment of such implants.

The detection of electrically isolated implants, however, is not without challenges. For example, even though the non-conductive coil 420 of FIG. 11 is intended to be electrically isolated from the joint 412, an undesirable situation may arise if coil 420 becomes conductive, such as when joint 412 comes into electrical contact with an implant or other conductive body already placed in the occlusion site, or if the electrically isolated coil 420 folds back on itself and contacts joint 412.

If this occurs, the monitored AC signal will drop to a clearly lower value corresponding to a new electrical circuit. While a drop in AC signal does not present a problem in and of itself, if the unintended contact is broken (returning the electrical circuit to its previous condition), the corresponding increase in AC impedance may be interpreted by the aforementioned known detachment detection systems (see, e.g., FIGS. 6–10) as coil detachment even though the coil may still be attached. Consequently, to be reliable, a detachment detection system must be capable of detecting detachment of electrically isolated implants, the more conventional conductive implants, and be capable of discerning non-detachment events from detachment events for both types of implants.

Detecting Detachment of Both Electrically Isolated and Conductive Implants

In accordance with the present invention, a dual-mode detachment detection apparatus and method is provided. Generally, the inventive detachment detection apparatus supplies and monitors an AC signal, sets a detachment threshold level based on whether the implant is conductive or non-conductive, and compares the monitored AC signal to the threshold level to determine whether the implant has detached. Additional safeguards are provided to ensure reliable detection including improvements to the power supply circuit, detection circuit, and power supply controller.

Figure 12:
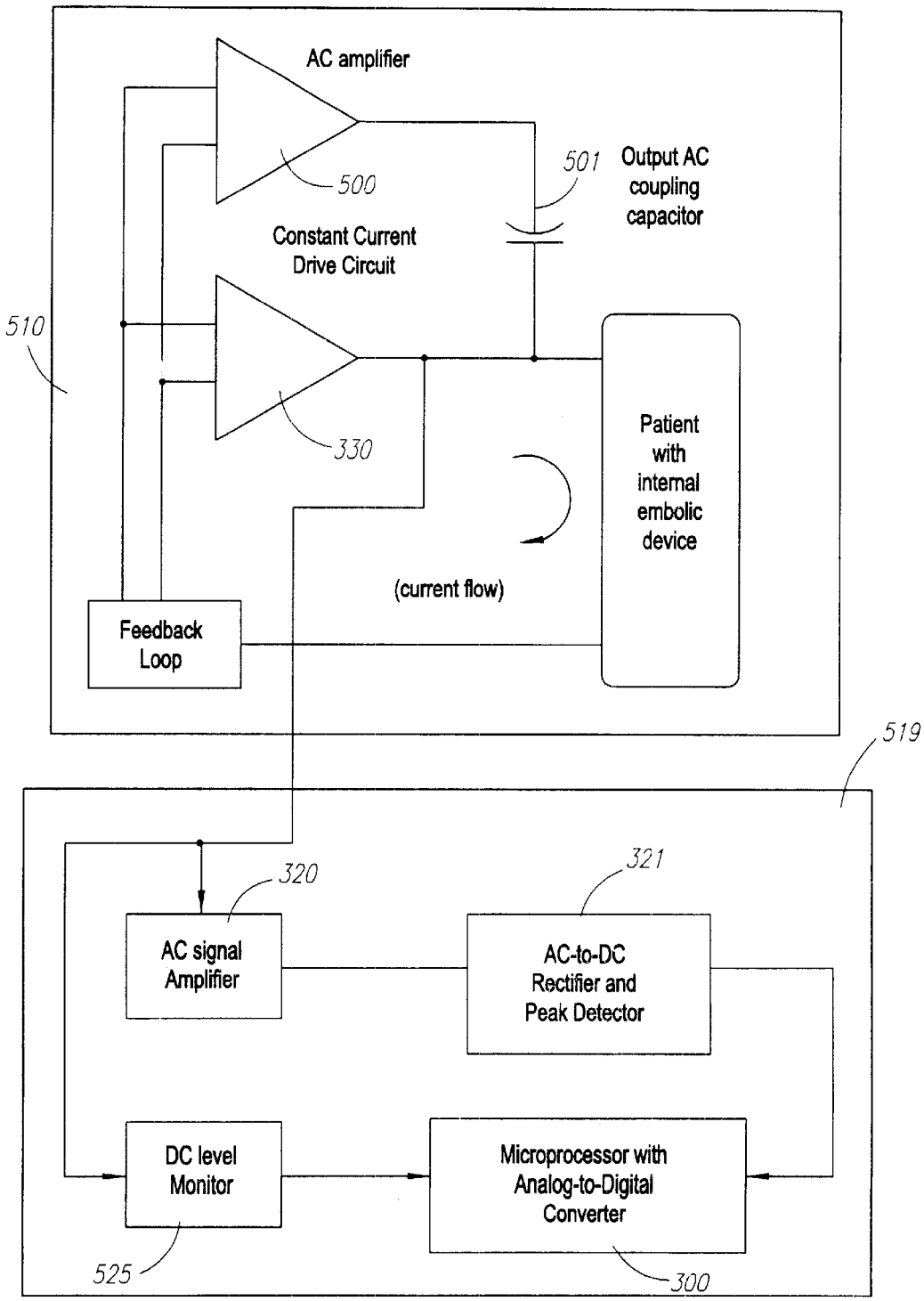
FIG. 12 is a block diagram of a power supply and detection circuit for detecting electrolytic separation of electrically conductive and electrically isolated vasoocclusive devices in accordance with the principles of the present invention.

As stated above, the inventive detection apparatus must first supply and monitor an AC signal. This circuitry is illustrated by the block diagram shown in FIG. 12 which is identical to FIG. 1. The block diagram of FIG. 12 depicts a power supply 510 and monitoring circuit 519. Power supply 510 supplies AC and DC power to the embolic device, and alternating current monitoring circuit or embolic device detection circuit (EDDC) 519 monitors the supplied AC and DC signal. Unlike the known examples described above, power supply 510 has independent AC and DC circuitry, described further below, which allows the AC signal to be independently monitored regardless of the DC signal. It has been found that independently supplying and monitoring the AC signal increases the reliability of detecting detachment of embolic devices including both electrically isolated and electrically conductive coils.

Figure 13:
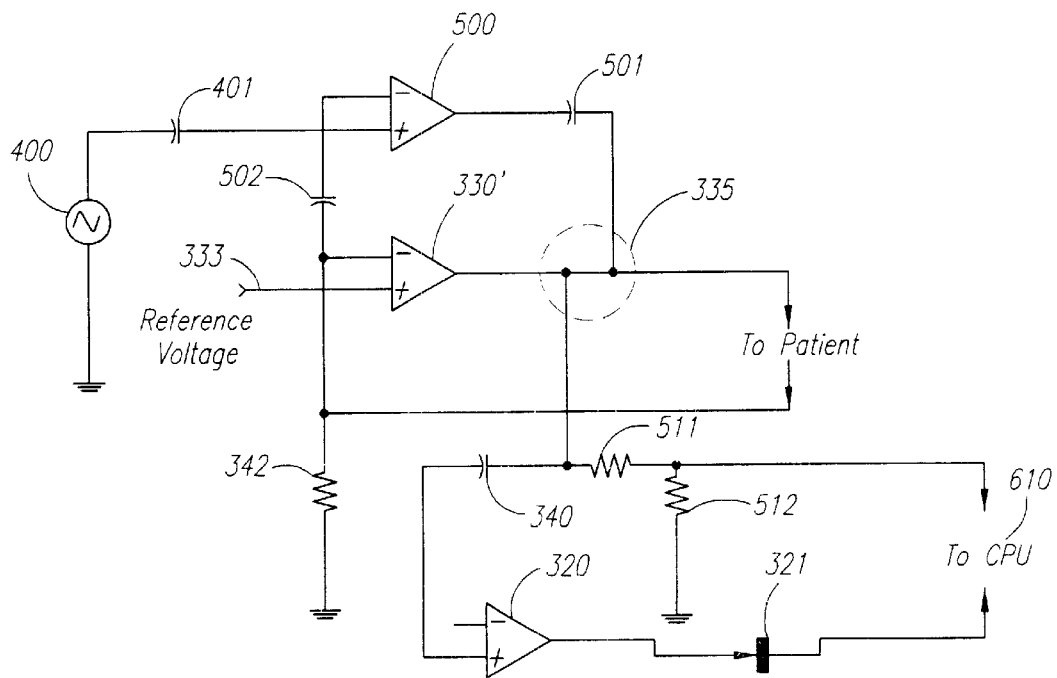
FIG. 13 is a schematic representation of the block diagram of FIG. 12

The independent nature of the AC and DC circuitry is illustrated with reference to FIG. 13. In FIG. 13, a sine wave generator 400 sends a sine wave (preferably, a 31.25 kHz sine wave) to the reference input of the EDDC amplifier 500, which is coupled via capacitor 501 to the output of the DC current-drive amplifier 330'. There, the AC signal is superimposed on the outgoing DC current, but separates in the patient when the DC current leaves the delivery wire at the detachment zone whereas the AC signal continues past the detachment zone, entering the patient's body at a location downstream of the detachment zone. This AC signal is used by the EDDC electronics to monitor the AC impedance of the patient loop and provides a primary method of coil detachment detection.

As illustrated in FIG. 13, the amplitude of the AC signal is monitored at the output connection 335 of the AC current-drive amplifier 500 and DC current-drive amplifier 330'. The amplitude of the AC signal is monitored through pick-off capacitor 340. The AC signal from capacitor 340 is then amplified in the AC signal amplifier 320, and is rectified and peak detected in the AC to DC rectifier 321. The DC signal from rectifier 321, the level of which is representative of the output amplitude of the AC voltage of current amplifier 500, is then sent to microprocessor or central processing unit (CPU) 610 for monitoring and analysis.

Coil Recognition Algorithm

As stated above, the detachment detection system of the present invention (an example of which is shown in FIGS. 12–15) accounts for detecting detachment of both conductive coils and electrically isolated coils. Depending on whether the coil is electrically conductive, a first mode or a second mode is selected to determine the threshold AC impedance level. The two modes also account for the possibility that an electrically-isolated or non-conductive coil could change states between non-conductive and conductive as previously discussed. Such an event effectively "shorts" the insulated junction or joint and the coil behaves as if it were a conventional conductive coil. If this conductive situation ends, such as by movement of the coil or core wire, the increase in monitored AC (or EDDC) level back to the normal non-conductive range could be interpreted by CPU 610 as an indication that coil detachment has occurred when in reality it has not.

In order to prevent changes in coil conductive states from triggering false detachment indications, CPU 610 reduces the EDDC sensitivity when a conductive coil is sensed. Essentially, CPU 610 raises the detachment threshold level to a fixed value when a coil is considered conductive.

Figure 14:
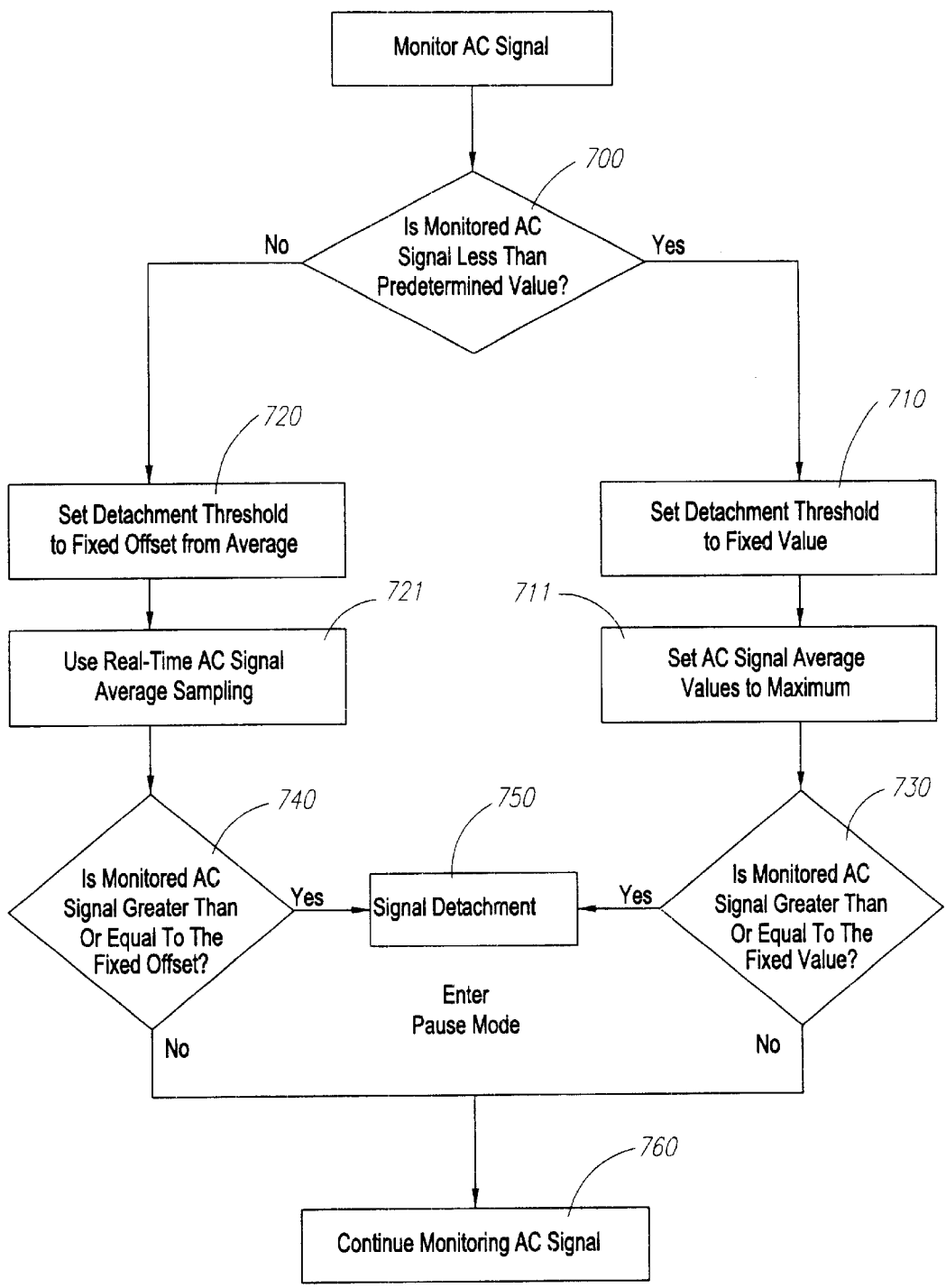
FIG. 14 is a flow chart illustrating steps of a coil recognition algorithm in accordance with the present invention.

To determine whether the coil is conductive, CPU 610 compares the monitored AC signal to a predetermined value as depicted by step 700 of FIG. 14. The coil is considered conductive if its monitored AC (or EDDC) level is below a predetermined value for a predetermined time period. The predetermined value ranges, for example, from about 0.7 to 2.5 VDC and is preferably equal to about 1.6 VDC. The predetermined time period ranges, for example, from about 0 to 5 seconds and is preferably about 0.5 seconds.

If a coil is considered to be in a conductive state (i.e., the EDDC level is less than the predetermined value for the predetermined time), the CPU 610 assigns the detection threshold level a fixed value (see e.g., step 710 of FIG. 14). The fixed value can range from about 3.0 V to 4.8 V and preferably is about 4.0 V. This fixed value is higher than the expected value for a non-conductive coil but can still be reached and surpassed when the coil actually detaches.

The calculation of an average EDDC level is halted during this period and the voltage readings used to calculate the average EDDC level are overwritten with maximum values to ensure that the calculated average level will be at maximum if the conductive state ends without detachment of the coil.

If the coil is a "shorted" electrically isolated or non-conductive device and the conductive situation ends, the sudden return of the EDDC level to a non-conductive value will not exceed the detachment threshold, and the DC and AC current will continue to flow.

If a coil is considered to be electrically isolated or in a non-conductive state (i.e., the EDDC level is greater than or equal to the predetermined value for the predetermined time period or a qualification time period), CPU 610 assigns the detection threshold level a fixed offset (see e.g., step 720 of FIG. 14). The fixed offset is a percentage or voltage increase over a running EDDC level averaged over a preceding nominal time period. The fixed offset may be about 0.1 V to 1.0 V and is preferably about 0.45V. The preceding nominal time period may be about 2 to 20 seconds and is preferably about 8 seconds.

If the coil was in a conductive state, and switches to a non-conductive state, CPU 610 switches from the first detection mode to the second detection mode after a qualification time period which may be about 0.0 to 2.0 seconds. At this time, CPU 610 begins updating the average EDDC level. Since the previous EDDC readings were overwritten with maximum values when the unit entered the first detection mode, the average EDDC level will drop to the actual average level over the course of the nominal averaging period, which in the preferred embodiment is about 8 seconds. The average level is forced to initialize at the maximum level to ensure that expected non-conductive EDDC levels do not cause false detachment indications when the second detection mode is activated.

Under either mode, however, detachment will only be indicated if the monitored AC signal is greater than the threshold level for a threshold or second predetermined time period. The threshold or second predetermined time period is about 0.2 to 2.0 seconds and preferably about 1.03 seconds.

Accordingly, if the CPU 610 detects such a change, it signals that the coil has detached (step 750 of FIG. 14) via a detach indicator 606 (FIG. 15) and enters a Pause Mode. If the increase in EDDC level does not remain valid for at least the threshold (second predetermined) time period, the CPU 610 ignores the event and current continues to flow to the coil until a stronger detachment indication is detected (see e.g., step 760 of FIG. 14). Thus, the detection system continuously monitors the coil regardless of whether the coil is conductive, and there is no limit to the number of times that a coil may change conductive states. Each time a coil becomes conductive, the threshold will be set to a fixed value and the average EDDC level readings will be overwritten with maximum values, and each time a coil becomes non-conductive, the threshold will be set to a fixed offset and the EDDC average level calculations will resume in real-time.

Once detachment is detected, the power supply enters a Pause Mode. In Pause Mode, CPU 610 preferably halts current flow, energizes the patient isolation relay 618 (FIG. 15), freezes the voltage, current and time displays, and indicates detachment with an appropriate signal using displays and preferably a beeper 621. For example, five beeps may be emitted from beeper 621, which can be a piezo transducer.

In Pause Mode, no further electrolysis occurs and the physician can verify under fluoroscopy that the coil has completely detached. If the coil is still attached, electrolysis can be resumed by pressing the current-select/resume switch 608. If the coil detachment is verified, the physician can turn off the power supply and remove the delivery wire. Another coil can be placed at the site, if necessary, and the power supply can be restarted. If no action is taken, the unit will automatically turn itself off after a given period (e.g., about 15 minutes) in Pause Mode.

DC Impedance Monitoring

In addition to the dual mode detection using the monitored AC impedance level as described above, the detection system of the present invention may also monitor DC impedance of the patient loop to detect coil detachment. In situations where the coil detaches and leaves no exposed material at the distal end of the delivery or core wire, the DC impedance will change. This DC impedance change results from the DC patient (or output) voltage increasing as the amplifier 330' of FIGS. 12–13 tries to maintain a set current through the patient. If a predetermined percentage increase in DC patient (or output) voltage occurs and remains for a specified (or third predetermined) time period and the EDDC level is above its threshold at the end of the DC qualification period (i.e., the specified or third predetermined time period), the system considers the event to be a coil detachment and immediately enters the Pause Mode. A percentage increase may be from about 20% to 60% and is preferably about 40%. A specified (or third predetermined) time period is from about 0.2 to 2.0 seconds and is preferably about 1.02 seconds.

The DC detection method, therefore, provides an additional monitoring system or safeguard that ensures that coil detachments are accurately detected. Premature detachment indications are rejected by both time-qualification of the DC signal and the need for EDDC confirmation. If the EDDC level is not above its threshold percentage increase when the DC qualification period ends, the unit does not signal detachment but performs a "rest cycle" to lower the DC impedance of the detachment zone.

Rest Cycle in Supply Of Direct Current

If the DC patient or output voltage suddenly increases without an increase in the EDDC level, the power supply will enter a "rest cycle." This condition may occur with an electrically isolated coil and is believed to be caused by temporary ion saturation at the detachment zone. Stopping the flow of electrolyzing current for a "rest cycle" (e.g., about two seconds or so) allows the ion saturation to dissipate and the patient impedance to drop. DC current can then be reapplied and the procedure will continue with coil detachment occurring in a normal fashion. One advantage of this feature is that if it were not implemented, the detachment time for that coil could be significantly longer.

When in the "rest cycle", the power supply stops the current flow and freezes the patient voltage and current displays for two seconds while the elapsed time display keeps counting. Normal operation resumes after the rest cycle has passed and the current begins ramping up to its previous level.

Power Supply Controller

Figure 15:
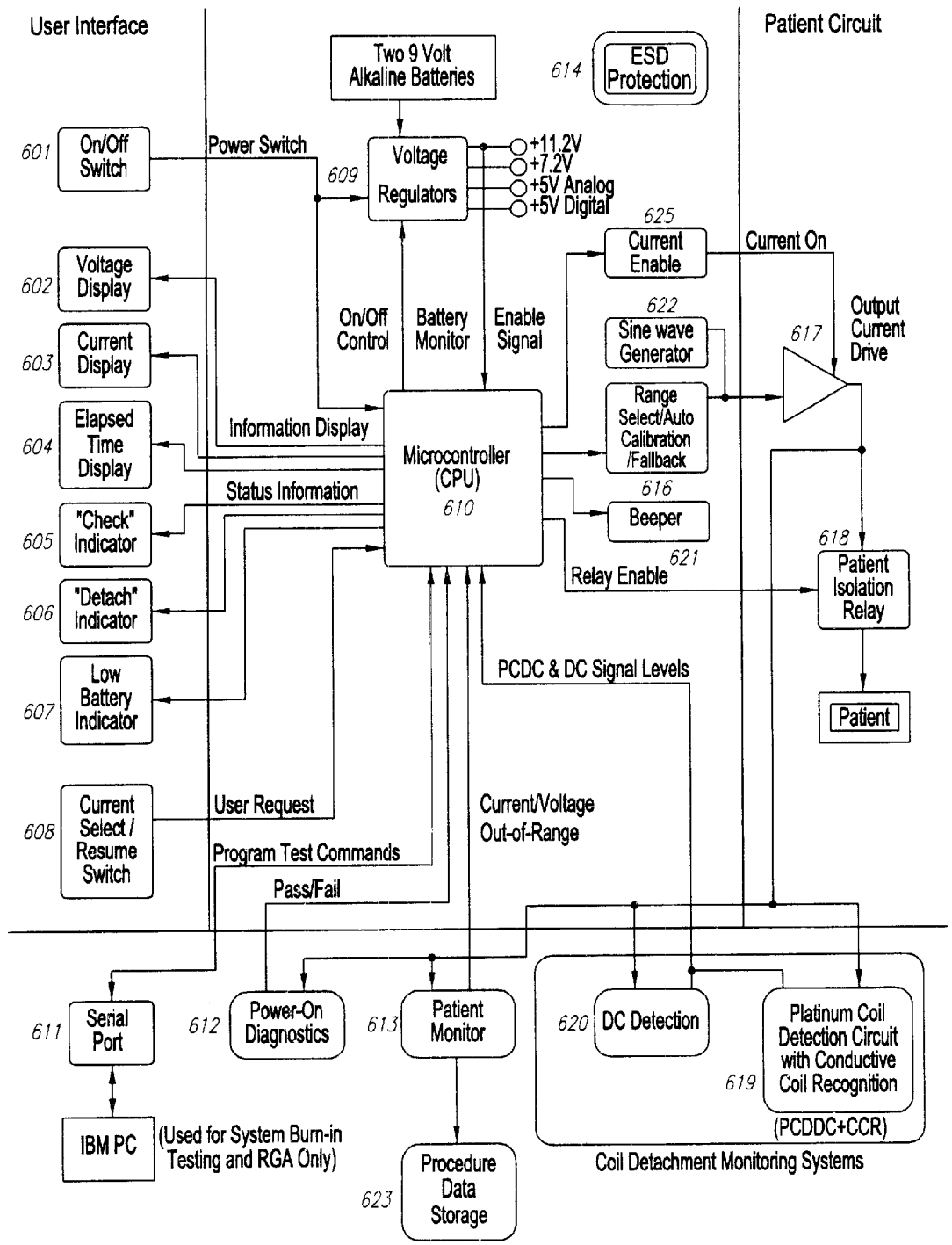
FIG. 15 is a block diagram showing the power supply and detection circuit of FIGS. 12–13 integrated with a power supply controller.

FIG. 15 shows a block diagram of a power supply controller integrated with the detection system described in FIGS. 12–14. While a description of the diagram, including description of particular features such as display characteristics follows, it should be understood that this description is provided for exemplary purposes and is not meant to limit the invention to the particular elements and arrangements discussed below.

Referring to FIG. 15, an on/off Switch 601 is used to activate the power supply. Voltage Display 602 displays the voltage used to maintain the constant current flowing (perhaps between about 0.00 to 2.25 mA) through the patient. The elapsed time display 604 displays the elapsed time from the start of the procedure.

A "check" indicator 605 signals the user if there is a poor connection between the power supply and patient at the beginning of each procedure (perhaps within the first six seconds after the on/off switch 601 is activated). A poor connection is typically caused by having one or both patient leads disconnected from the pusher wire or return electrode, or when the coil junction or joint remains inside the catheter. The check indicator 605 will remain on until the condition is corrected or the unit is shut off. If the poor connection is corrected while the unit is running, the check indicator 605 will deactivate, the current will begin ramping up to its expected level and the procedure will proceed normally.

A "detach" indicator 606 signals that the power supply is no longer supplying power to a coil, e.g., after a coil detachment. Low battery indicator 607 signals when the internal battery voltage drops below an appropriate level.

The current-select/resume switch 608 works to change the patient current setting. Each time the power supply is turned on, the current is set to an appropriate level such as 1.00 mA. Pressing the switch changes the setting to another level. In Pause Mode, pressing this switch will resume current flow to the coil.

Voltage regulators 609 provide +7.2 volts, analog +5 VDC and digital +5 VDC. The +7.2 volt rail is then converted by a DC/DC converter to +11.2 V for use by the output amplifier. Microcontroller (CPU or MCU) 610 will be reset by hardware if the digital +5 V power supply drops below 4.8 VDC. Two Schottky diodes (one in series with each battery, not shown) provide protection and isolation from reversed battery conditions.

Electrostatic discharge protection 614 may be provided by, for example, metal oxide varistors (MOVs). In this variation, the MOVs shunt any voltage higher than 12 volts to battery ground to protect the electronics. One MOV may be placed from each patient terminal to battery ground to protect the output amplifiers and patient from static discharge. Additional radio frequency interference (RFI) noise may be suppressed using various resistor/capacitor configurations. A MOV across the power switch and one across the current-select switch protect the power supply from surges entering through the switch contacts. A MOV may be placed across each battery, and a final MOV may be placed across the digital +5 V power rail to protect internal components from static-induced power surges.

The "current enable" circuit 615 preferably requires an active square wave signal from the CPU 610 to start and maintain patient current. If anything happens to the CPU 610, or if the program stops running normally, the active signal will cease or become infrequent. The patient current will then be automatically shut off by this fail-safe current shutdown circuit.

The current range select/fallback circuit 616 may use a solid state digital potentiometer controlled by the CPU 610 to set the desired output current. This eliminates the need for factory calibration, and the unit compensates for any variations in the output current set point each time it is turned on. During the auto calibration sequence, the patient isolation relay 618 is energized to prevent the calibration voltage and current from reaching the patient and the current drive circuit is enabled.

Automatic Current Fallback and Ramp Up

If the DC impedance is too high to maintain a constant controlled current (e.g. about 2.00 mA) during a detachment procedure, the CPU 610 automatically reduces the output current to a lower value (e.g., about 1.00 mA) by changing the 'position' of the digital pot. This adjustment or "current fallback" of the current to about 1.00 mA ensures that there is enough voltage to supply the patient current in a controlled manner. No physician intervention is required. The physician has the option to increase the current again at any time following a current fallback.

The current may be gradually ramped up at, for example, (1) the start of each procedure, (2) when the current range is changed, or (3) upon lead connection after a procedure has been started without the leads in place to avoid sudden current changes through the patient.

The output current circuit 617 requires an active signal from the current-enable circuit 615 to turn on and remain on. The output drive circuit 617 is a constant current source that will apply as much voltage as necessary to maintain the required patient current. The maximum voltage is limited to approximately +11 volts DC, with zero as the minimum output voltage. The patient current and voltage are displayed in real time on the front panel voltage and current displays.

The patient isolation relay 618 disconnects the patient leads during the power up diagnostics, after a coil has detached, and if a failure occurs during a procedure. When the patient isolation relay 618 is energized, the patient is electrically disconnected from the power supply and an internal load is placed across the output drive circuit. During power up testing, the normal current-ramping feature is bypassed to allow the CPU 610 to quickly perform the power up current and EDDC level calibration and the voltage level tests. The relay prevents patient exposure to the calibration voltages and currents. When the power supply is in Pause Mode after a coil detachment, the current drive circuit is disabled and the energized relay ensures that no further electrolysis can occur. In the case of a system failure, both patient leads are automatically disconnected from the internal power circuitry to keep the patient from being exposed to possible unintended voltage or current levels.

Automatic Calibration of the Detection System

Each time the power supply is activated, the patient isolation relay 618 is energized (isolating the patient) and the CPU 610 is capable of running a number of diagnostic tests including a RAM test, program integrity Erasable Programmable Read Only Memory (EPROM) test, output current calibration and voltage validation, EDDC level calibration, fail-safe current-shutdown test, and a patient-isolation relay fail test. If this optional feature is included, only if all tests are passed does the unit begin normal operation. A failure of any test results in the electrical isolation of the patient from the power supply and an error message displayed on any number of the previously described indicators.

The RAM test verifies that every single byte of RAM is functional by writing and verifying two sets of complementary values at each location. All address lines are individually verified to ensure that none are stuck at '0' or '1.' The program will continue only if all bytes and address lines pass these tests. Otherwise, the CPU 610 halts the start-up procedure and can display an appropriate message using the indicators.

The program integrity EPROM test adds together all of the programmed (used) bytes of the EPROM to calculate a checksum. This value is compared to the checksum also stored in the EPROM. If any one of the tens of thousands of bits in the EPROM is different from the value originally programmed, the CPU 610 halts the startup procedure and may display an appropriate message on indicators or signal with an equivalent indicator.

The patient current test verifies that the patient current flowing through the internal test load is accurately calibrated. During the auto calibration sequence, the CPU 610 verifies that it can adjust the patient current to, for example, 0.50 mA, 1.00 mA and 2.00 mA with an accuracy of preferably within ±1%. If the current cannot be adjusted to these levels, the CPU 610 halts the start-up procedure and indicates failure on the displays.

The patient voltage test monitors the voltage across the internal test load during the auto calibration sequence and verifies that the voltage is within 5% of the specified value at, for example, 0.50 mA, 1.00 mA and 2.00 mA. If a deviation of more than ±5% is detected, the CPU 610 halts the start-up procedure and may display an appropriate message on the indicators or like displays.

The patient current and voltage are also continuously measured by the patient monitoring circuitry 613 during every procedure. If the current ever deviates more than about 5% above the set point, or about 5% below nominal and the voltage is below about 9.25 V, the CPU 610 shuts down. Low current with high voltage (called voltage-limited operation) commonly occurs after coil detachment, when there is a bad connection, and in certain situations with non-conductive coils. This does not represent an error condition and the power supply proceeds normally under these conditions. If the power supply continues in a voltage-limited condition for about 3 seconds and the current is set to e.g., 2.00 mA, a "current fallback" will occur which automatically reduces the current to e.g., 1.00 mA. If the power supply is voltage-limited for more than about 4 seconds and the current is already at or below about 1 mA, a detachment indication will be issued. Also, if the output voltage ever goes above about 11.7 volts, the CPU 610 reports and shuts down immediately.

The EDDC system test verifies that the EDDC signal can be calibrated within about 4% of the optimum value of about 3.75 VDC when it runs through the internal self-test load. If the level cannot be adjusted to an accuracy of ±4%, the CPU 610 halts the start-up procedure and may display such EDDC failure on the displays.

The current shutdown test verifies that the current drive circuitry shuts down when the 'current enable' signal from the CPU 610 is disabled. The worst case failure condition is simulated to verify that the hardware shuts down. If a problem occurs, the CPU 610 halts the start-up procedure and displays output failure on the displays.

The patient isolation relay test verifies that the patient isolation relay 618 is correctly connected to the patient after all the diagnostic tests have been run. If the relay is stuck in the internal test position, the CPU 610 halts the start-up procedure and indicates such on the displays.

Central Processing Unit

The CPU 610 may preferably be a Motorola series 68HC11 single-chip microcontroller or the like. CPU 610 controls and monitors vital functions of the power supply. Every time the power supply is activated, the CPU 610 runs a number of self-diagnostic tests including, e.g., the automatic calibration procedures described above. The CPU 610 is responsible for monitoring the input battery voltage, output (patient) current, voltage and EDDC level, as well as the elapsed time during every procedure. The CPU also manages the displays, status indicators and beeper, controls the fail-safe current enable signal, and monitors the EDDC and Direct Current signals to determine when coil detachment has occurred. In addition, the CPU 610 monitors the current-select/resume switch 608, and is capable of communicating with a remote computer or the like via a serial or other port 611.

An on-board timer forces a procedure restart if CPU 610 strays from its intended program. CPU 610 may be tested and queried by a remote computer or the like via an internal serial port 611, such as a 4800 baud RS-232 connection.

A data recorder 623 is provided and may be a single chip, nonvolatile XICOR serial EEPROM. Such a recorder 623 can store, for example, the most recent procedural data taken while the system is running. The most recent data may be data from the preceding 2 to 20 minutes and preferably, the most recent data from the preceding 8.5 minutes. Examples of the type of procedural data include: elapsed time, patient current, patient voltage, EDDC level, DC and EDDC detachment threshold levels, as well as the detachment, rest cycle and battery status. Preferably, the newest data overwrites the oldest data which can be implemented in a first-in first-out (FIFO) configuration. Data collection stops after about 2 seconds in Pause Mode, and resumes along with the current if the physician presses the current-select/resume switch 608. Data collection also stops when the unit is shut off.

There is no limit or specification as to how many different implant detachments are included in the most recent data. As such, the stored data might contain only the last 8.5 minutes of a long detachment procedure or as many as two dozen rapid coil detachments spread over several patients.

The data is preferably stored in a non-volatile device which allows the later retrieval of said data even if the batteries run down or are removed.

The implant detachment detection apparatus and method have been described with reference to specific embodiments for the purposes of illustration and should not be taken as limiting the invention. Many alterations and modifications may be made by those having ordinary skill in the art without departing from the spirit and scope of the invention as defined by the following claims.

What is claimed is:

1. An implant detachment detection assembly comprising:
   an implant member having a proximal end;
   a wire having an electrolytically severable joint, said wire being connected to the implant member proximal end, wherein said implant is electrically isolated from said joint; and
   a power supply comprising a direct current drive circuit for supplying a direct current to said joint, an alternating current drive circuit for supplying an alternating current to said joint, and an alternating current monitoring circuit for monitoring an alternating current level of said alternating current supplied to said joint.

2. The detection assembly of claim 1 further comprising a microprocessor for selecting a first mode and a second mode for determining detachment of the implant, whereby said first mode is selected when said alternating current level is less than a predetermined value for a first predetermined time period and said second mode is selected when said alternating current level is greater than or equal to said predetermined value for a qualification time period.

3. The detection assembly of claim 2 wherein each of said first mode and said second mode assigns a detachment threshold level for indicating detachment of said implant when said alternating current level is greater than said detachment threshold level for a second predetermined time period.

4. The detection assembly of claim 3 wherein said detachment threshold level assigned by said first mode is a fixed value.

5. The detection assembly of claim 3 wherein said detachment threshold level assigned by said second mode is a fixed offset.

6. The detection assembly of claim 2 further comprising a direct current monitoring circuit for monitoring a direct current impedance level of said direct current supplied to said joint, wherein a percentage increase in the direct current impedance level for more than a third predetermined time period indicates detachment of the implant if said alternating current level is greater than said detachment threshold level.

7. The detection assembly of claim 6 wherein said microprocessor interrupts said direct current for a fourth predetermined time period when said direct current impedance level increases without an increase in said alternating current level.

8. The detection assembly of claim 1 further comprising means for automatically calibrating said alternating current monitoring circuit when said detection assembly is activated.

9. The detection assembly of claim 1 wherein said alternating current drive circuit operates independently of said direct current drive circuit.

10. The detection assembly of claim 1 further comprising a recorder for storing data.

11. The detection assembly of claim 1 wherein said alternating current supplied by said alternating current drive circuit is relatively constant and said monitored alternating current level is a voltage.

12. The detection assembly of claim 1 further comprising a number of discrete electronic components for selecting a first mode and a second mode for determining detachment of the implant, whereby said first mode is selected when said alternating current level is less than a predetermined value for a first predetermined time period and said second mode is selected when said alternating current level is greater than or equal to said predetermined value for a qualification time period.

13. A method for detecting electrolytic detachment of a vasoocclusive implant from a wire comprising:

determining a threshold level for indicating detachment of said vasoocclusive implant when a monitored alternating current impedance level is greater than said threshold level for a threshold time period, said threshold level being determined under a first mode if said monitored alternating current impedance level is less than a predetermined value for a predetermined time period and said threshold level being determined under a second mode if said monitored alternating current impedance level is greater than or equal to said predetermined value for a qualification time period; and comparing said monitored alternating current impedance level to said threshold level.

14. The method of claim 13 wherein said first mode assigns a fixed value to said threshold level.

15. The method of claim 13 wherein said second mode assigns a fixed offset to said threshold level.

16. The method of claim 13 further comprising measuring a direct current impedance level of a direct current supplied to an electrolytically severable joint, said joint joining said wire and said vasoocclusive implant, wherein a percentage increase in said direct current impedance level for more than a specified time indicates detachment of said vasoocclusive implant if said monitored alternating current impedance level is greater than said threshold level.

17. The method of claim 16 further comprising the step of interrupting said direct current when said direct current impedance level increases without an increase in said monitored alternating current impedance level.

18. The method of claim 13 wherein said vasoocclusive implant is an electrically isolated coil.

19. The method of claim 13 wherein said monitored alternating current impedance level is a voltage.

20. A power supply for supplying a direct current to a wire having an electrolytically severable joint, said power supply comprising:

a direct current drive circuit for supplying said direct current to said electrolytically severable joint;

an alternating current drive circuit for supplying an alternating current to said joint, said alternating current drive circuit operating independently of said direct current drive circuit;

an alternating current monitoring circuit for monitoring an alternating current impedance of said alternating current supplied to said joint; and a selecting means for selecting a threshold level and for indicating detachment of a vasoocclusive implant from said joint when said alternating current impedance is greater than said threshold level for a threshold time period.

21. The power supply of claim 20 wherein said selecting means selects a fixed threshold level when said alternating current impedance is below a predetermined value for a predetermined time period and said microprocessor selects a fixed offset threshold level when said alternating current impedance is greater than or equal to said predetermined value for a qualification time period.

22. The power supply of claim 20 wherein said selecting means automatically reduces said direct current if said direct current drive circuit cannot maintain a relatively constant direct current during operation.

23. The power supply of claim 20 wherein said direct current is gradually changed to a specified amount.

24. The power supply of claim 23 wherein said direct current is gradually increased to said specified amount after the start of a procedure.

25. The power supply of claim 20 further comprising means for automatically calibrating said alternating current monitoring circuit when said power supply is activated.

26. The power supply of claim 20 further comprising a direct current monitoring circuit for measuring a direct current impedance of said direct current supplied to said electrolytically severable joint, wherein a percentage increase in said direct current impedance indicates detachment of said vasoocclusive implant if said alternating current impedance is greater than said threshold level.

27. The power supply of claim 26 wherein said selecting means interrupts said direct current when said direct current impedance increases without an increase in said alternating current impedance.

28. The power supply of claim 20 further comprising a recorder for storing data.

29. The power supply of claim 20 wherein said implant is electrically isolated from said joint.

30. The power supply of claim 20 wherein said alternating current supplied to said joint is relatively constant and said alternating current impedance is monitored as a voltage.

31. The power supply of claim 20 wherein said selecting means comprises a number of discrete electronic components.

32. The power supply of claim 20 wherein said selecting means comprises a microprocessor.

33. An implant detachment detection assembly comprising:

an implant member having a proximal end;

a wire having an electrolytically severable joint, said wire being connected to said implant member proximal end, wherein said implant is electrically isolated from said joint;

a power supply comprising a direct current drive circuit for supplying a relatively constant direct current to said joint, an alternating current drive circuit for independently supplying a relatively constant alternating current to said joint, an alternating current monitoring circuit for monitoring an alternating current voltage of said alternating current supplied to said joint;

a central processing unit for selecting a first mode and a second mode for determining a detachment threshold voltage for indicating detachment of the implant, said first mode selected when said alternating current voltage is less than a predetermined voltage for a first predetermined time period and said second mode selected when said alternating current voltage is greater than or equal to said predetermined voltage for a qualification time period, wherein said detachment threshold voltage is set to a fixed values voltage under said first mode and said detachment threshold voltage is set to a fixed offset voltage under said second mode; and a direct current monitoring circuit for measuring an output voltage of said direct current drive circuit, wherein a percentage increase in said output voltage indicates detachment of said implant if said alternating current voltage is greater than said detachment threshold voltage.

* * * * *

UNITED STATES PATENT AND TRADEMARK OFFICE
CERTIFICATE OF CORRECTION

PATENT NO. : 6,397,850 B1
DATED : June 4, 2002
INVENTOR(S) : Ronald W. Scheldrup, Jason E. Kalgreen and Mehran Bashiri It is certified that error appears in the above-identified patent and that said Letters Patent is hereby corrected as shown below:

<u>Title page,</u>
Please insert Item: -- [73] Assignee: Scimed Life Systems, Inc., Maple Grove, MN --

Signed and Sealed this

First Day of July, 2003

JAMES E. ROGAN
*Director of the United States Patent and Trademark Office*